United States Patent [19]

Michl

[11] Patent Number: 4,599,462
[45] Date of Patent: Jul. 8, 1986

[54] METHODS FOR MAKING SOLID SOLUTIONS FROM NORMALLY IMMISCIBLE COMPONENTS AND FOR MODIFYING THE SURFACE STRUCTURE OF SOLID MATERIALS

[75] Inventor: Josef Michl, Salt Lake City, Utah

[73] Assignee: University of Utah, Salt Lake City, Utah

[21] Appl. No.: 497,789

[22] Filed: May 25, 1983

[51] Int. Cl.$^4$ .................. C07C 37/88; C07C 37/68
[52] U.S. Cl. .................................... 568/702; 62/10;
252/380; 252/383; 252/393; 427/255.2;
568/716; 568/775
[58] Field of Search ............ 62/10, 45; 568/702,
568/701, 716, 775; 427/255.2; 585/1, 2; 422/41,
42; 252/383, 393, 380

[56] References Cited

U.S. PATENT DOCUMENTS 4,190,016 2/1980 Hendricks ........................ 62/10

OTHER PUBLICATIONS

Jones, "Chemical Abstracts", vol. 78, (1973) p. 140781r.
Sato et al., "Chemical Abstracts", vol. 91(17) p. 140123w (1979).
Podlesski et al., "Chemical Abstracts", vol. 87(22) p. 173616e.
B. M. Chadwick, "Matrix Isolation," 6, *Molecular Spectroscopy*, 72–135 (1979).
*Vibrational Spectroscopy of Trapped Species*, (H. E. Hallam ed. 1973), Pub. by Wiley & Sons, NY, London.
J. R. Brailsford & J. R. Martin, "Paramagnetic Resonance Spectra of NO$_2$ Trapped in Alkali Halides," 1, *Journal of Magnetic Resonance*, 575–583 (1969).
*Polycrystalline and Amorphous Thin Films and Devices*, (L. L. Kazmerski ed. 1980).
H. Bartels & B. Prijs, "Specifically Adsorbing Silica Gels," *Advances in Chromatography*, 115–143 (1974).
*Cryochemistry* (M. Moskovits & G. A. Ozin ed. 1976).
A. J. Downs & S. C. Peake, "Matrix Isolation," 1, *Molecular Spectroscopy*, 523–607 (1973).
B. M. Chadwick, "Matrix Isolation," 3, *Molecular Spectroscopy*, 281–382 (1975).
C. L. Chien et al., "Magnetic Hyperfine Interactions in Amorphous Fe$_x$ B$_{100-x}$," 25, Physical Review B, 5790–5796, No. 9 (May 1982).
F. R. Gamble et al., "Enhancement of the Critical Temperature of Aluminum by Molecular Inclusions," 26A, Physics Letters, 162–163, No. 4, (Jan. 1968).
H. M. McConnell et al., "Interactions Between Superconductors and Organic Molecules," 57, Proceedings of the National Academy of Science, 1131–1137, No. 5, (May 1967).

Primary Examiner—Werren B. Lone
Attorney, Agent, or Firm—Workman, Nydegger & Jensen

[57] ABSTRACT

Novel composites or solid solutions made from heretofore immiscible chemical components and methods for making such composites or solid solutions. A wall of a deposition cell is cooled to a temperature within the range of about −273° C. to about −20° C. A solid host component and one or more guest components are vaporized and codeposited onto the cold wall of the deposition cell so as to form a solid solution. The resultant solid solutions are stable at room temperature and often at much higher temperatures. The present invention also provides methods for modifying the surface structure of solid materials.

40 Claims, 4 Drawing Figures

METHODS FOR MAKING SOLID SOLUTIONS FROM NORMALLY IMMISCIBLE COMPONENTS AND FOR MODIFYING THE SURFACE STRUCTURE OF SOLID MATERIALS

BACKGROUND

1. The Field of the Invention

The present invention relates to composite materials and methods for making such materials, and in particular, to solid solutions of chemical components which are not appreciably miscible under equilibrium conditions. The present invention further relates to methods for modifying the surface structure of solid materials.

2. The Prior Art

In the preparation of chemical solutions, whether in the gaseous, liquid, or solid state, the mutual solubility or miscibility of the chemical components which are to form the solution is extremely important. Two chemicals which are relatively immiscible (and thus relatively insoluble) with respect to each other can generally not form a homogeneous solution having the desirable proportions of each component which would be needed to provide the chemical benefits of each component.

Often, it is desirable to form solid solutions of different chemical components. (As used herein, the term "solid solution" refers to a solution in which one or more chemical components (whether normally solid, liquid, or gas at room temperature) are dispersed throughout a solid host component or medium.) If the solid host medium and the chemical components which are desired to be dispersed therein are found to be immiscible using known techniques, such solid solutions have heretofore been impossible to form. Thus, there exists a large number of desirable yet heretofore merely hypothetical solid solutions which have not been prepared because of the immiscibility of the particular chemical components with respect to the solid host medium when conventional techniques have been used.

The utility of such "hypothetical" solid solutions would be enormous. For example, many compounds exist which are unstable in air, have bad odors, are toxic, are highly reactive or corrosive, are flammable, or are explosive in bulk. It would be extremely useful to isolate such compounds in a solid host medium which is relatively inert with respect to these compounds so as to form a solid solution; in such a solid solution, these compounds would be preserved in isolation for later use. Such isolation in the solid host medium would serve, for example, to increase the stability of these compounds upon exposure to air, to mask their bad odors, to control their toxicity, to prevent their premature or corrosive reaction with other substances or with themselves, to control their flammability, or to prevent their explosion.

Very little has been done in the prior art to develop methods whereby normally immiscible components may be combined to form a solid solution. One method used in the prior art to create unusual solid solutions involves inert gas matrices. Frozen inert gas matrices have been used to isolate various chemical species within a solid matrix so as to allow for study of the isolated species and/or its response to different stimuli. The formation of inert gas matrices is accomplished by codepositing the species to be isolated and the inert gas (which acts as the solid host medium) onto a cold wall under vacuum.

A typical procedure for forming an inert gas matrix is as follows: One or more chemical species to be isolated (e.g., a metal) is vaporized and introduced at a cold wall concurrently with an excess amount of an inert gas (typically argon). The cold wall is maintained at a temperature well below the freezing point of the inert gas (typically about 4–20K), so that the inert gas will exist in a solid state. Thus, upon codeposition of the species to be isolated with an excess of the inert gas onto the cold wall, a solid matrix is formed wherein the isolated species is dispersed throughout the solid argon. Typically, the species to be isolated is deposited with the inert gas onto the cold wall in a molar ratio of at least about 100:1 (inert gas:isolated species) to well above 1000:1.

In addition to argon, other host media have occasionally been used in such low temperature matrices, including xenon (Xe), nitrogen ($N_2$), methane ($CH_4$), sulfur hexafluoride ($SF_6$), carbon monoxide (CO), and pentane ($C_5H_{12}$). A substantial drawback of these prior art low temperature matrices if the fact that these matrices can only exist at temperatures where the host medium remains in a solid state; this means that for most of the widely-used matrices, the temperature is maintained below about 50K. Thus, the prior art matrices have been extremely limited in the temperatures at which the matrices could be constructed, observed, and preserved for later use. The result has been that the practical use of these low temperature inert gas matrices has been extremely limited; indeed, the only real use has been to provide a means to scientifically study the spectroscopy of the isolated component under these extreme temperature conditions.

Solid solutions of the prior art which may exist at room temperature include inclusion compounds, which typically comprise a solid material which is porous to a vapor component. The solid material and vapor component are miscible, and the vapor component continually enters and exits the solid material in an equilibrium situation which is determined, to a large extent, by the pressure of the vapor component outside of the solid material. Thus, in the prior art inclusion compounds, the vapor components are not trapped within the solid material in a fixed state, but rather move in and out of the solid material according to the principles of chemical equilibria.

In the prior art, thin layers of metal alloys have been vapor deposited at room or high temperatures, typically on a heated surface significantly above room temperature. Such high temperature deposition is often important in forming these metal alloy thin layers. For instance the high temperatures provide for good epitaxial growth and increased translation of the metal components within each other so as to enhance the desirable properties of the thin layers produced.

From the foregoing, it will be appreciated that it would be a significant advancement in the art if novel solid solutions of heretofore immiscible chemical components could be prepared and especially solid solutions which are stable at temperatures greater than 50K. It would be a further significant advancement in the art to provide a method for forming novel solid solutions from heretofore immiscible chemical components wherein the solid solutions are stable at room temperature, and often much higher temperatures, so as to allow the solid solutions to be used in a greater variety of applications. For example, it would be an advancement in the art to provide such solid solutions for isolating and preserving chemical components which are unstable in air, have bad odors, are toxic, are highly reactive, or are explosive in bulk. Such solid solutions and methods for forming these solid solutions are disclosed and claimed herein.

BRIEF SUMMARY AND OBJECTS OF THE INVENTION

The present invention relates to novel composites or solid solutions made from heretofore immiscible chemical components, and to methods for making such composites or solid solutions. The present invention also relates to methods for modifying the surface structure of solid materials.

To form the novel solid solutions of the present invention, a deposition substrate is cooled to a temperature within the range of about $-273°$ C. to about $-20°$ C., depending on the particular chemical components to be deposited thereon. A host component, which is to provide the solid host medium for the solid solution, and one or more guest components to be included into the solid solution are vaporized. The vaporized host component and the vaporized guest components are then codeposited onto the cold substrate so that the host component and the guests components condense on the cold substrate to form a solid solution.

Preferably, the host component comprises a chemical compound which is a solid at room temperature or even much higher temperatures. The guest components comprise chemical compounds which may be solids, liquids, or gases at room temperature, and which are typically immiscible with the host component according to conventional techniques. The resulting solid solution is stable at room temperature and pressure, and often at much higher temperatures, even temperatures above the typical vaporization temperature of the guest components.

The present invention thus provides methods for making solid solutions which have heretofore not been possible using standard techniques. As a result, a vast number of chemical compounds may be isolated and preserved within these solid solutions for later release, use, transformation, or examination. Importantly, the solid solutions of the present invention are stable at temperatures near room temperature, and often temperatures much higher; the result is that the solid solutions of the present invention have significantly more utility than the prior art low temperature inert gas matrices.

It is, therefore, an object of the present invention to provide novel solid solutions which have been heretofore unknown and to provide methods for making the same.

Another object of the present invention is to provide methods for preparing solid solutions from chemical components which have generally been considered to be immiscible according to conventional techniques.

Still another object of the present invention is to provide solid solutions made of heretofore immiscible chemical components which are stable at room temperature and pressure, and often much higher temperatures, and to provide methods for making such solid solutions.

Yet another object of the present invention is to provide methods for isolating and preserving compounds for subsequent release, use, transformation or examination, including compounds which are unstable in air, have bad odors, are toxic, are highly reactive or corrosive, are flammable, or are explosive in bulk.

A further object of the present invention is to provide methods for modifying the surfaces of solid materials so as to modify chemical and physical properties of the solid materials, such as adsorption properties.

These and other objects and features of the present invention will become more fully apparent from the following description and appended claims, taken in conjunction with the accompanying drawings.

DETAILED DESCRIPTION OF THE PREFERRED EMBODIMENTS

Reference is now made to the drawings wherein like parts are designated with like numerals throughout. While it will be appreciated that many different types of apparatus may be used to practice the present invention, one presently preferred embodiment of an apparatus, generally designated 10, which may be used in produce the composites or solid solutions of the present invention, is illustrated in FIG. 1.

Figure 1:
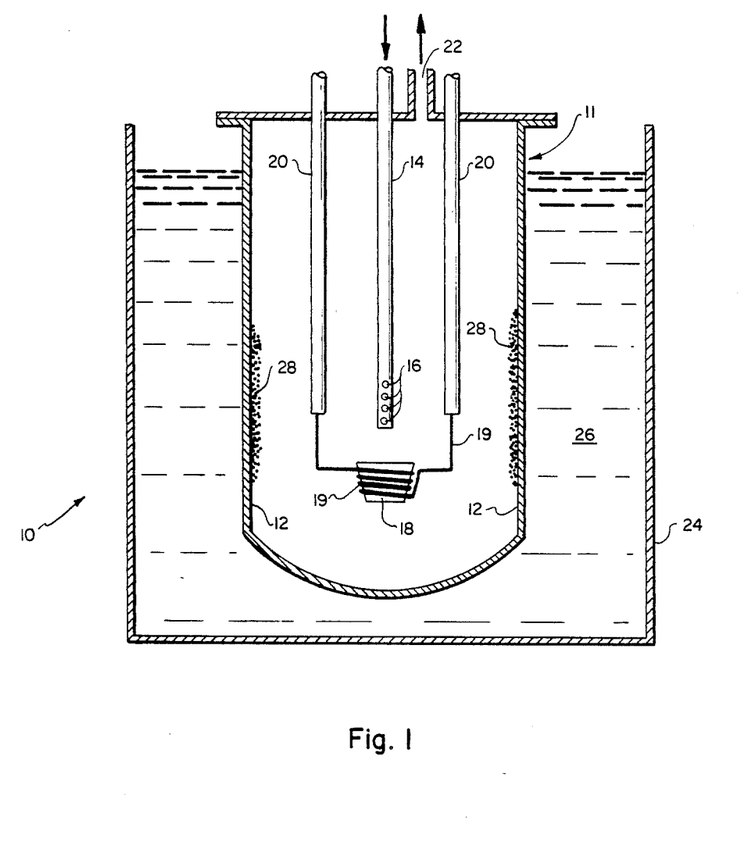
FIG. 1 illustrates a presently preferred embodiment of an apparatus which may be used to prepare composites and solid solutions in accordance with the method of the present invention.

Referring to FIG. 1, apparatus 10 includes a deposition cell, generally designated 11, immersed in a cold temperature bath 26 within an insulated vessel 24. Deposition cell 11 has a wall 12 upon which deposition of the solid solutions of the present invention may be achieved.

Extending into deposition cell 11 is a vapor supply conduit 14 having a plurality of apertures 16 formed therein. Vapor supply conduit 14 provides for the introduction of one or more vaporized chemical guest components into deposition cell 11. Means (not shown) may be provided for heating vapor supply conduit 14 so as to vaporize those guest components which are not gases at room temperature. Further disposed within deposition cell 11 is a crucible 18 for receiving a solid chemical component to be vaporized. Crucible 18 is suspended within the deposition cell by two water-cooled electrodes 20 which are connected to crucible 18 by a heating element 19. Heating element 19 is wound around crucible 18 and serves to heat the crucible upon activation of electrodes 20 so as to vaporize the solid sample within crucible 18. A vacuum port 22 is formed at the top of deposition cell 11 and allows for evacuation of the interior of deposition cell 11 by a vacuum pump (not shown).

The operation of apparatus 10 and one presently preferred method for making the solid solutions of the present invention are best understood from the following discussion. Cold temperature bath 26 is prepared by introducing an appropriate cold temperature medium into vessel 24. Generally, for purposes of the present invention, cold temperature bath 26 should be of a temperature within the range of about −273° C. to about −20° C. The exact preferred temperature of cold temperature bath 26 will, of course, depend upon the particular chemical components to be deposited into a solid solution along wall 12 of deposition cell 11. Clearly, it is critical that wall 12 be cold enough to accommodate such a deposition.

Cold temperature media which have been found suitable for preparing cold temperature bath 26 include, for example, a three molar (3M) solution of calcium chloride ($CaCl_2$) in an ice-water bath (−22° C.), a dry ice/acetone ($CO_2/CH_3COCH_3$) bath (−77° C.), and a liquid nitrogen ($N_2$) bath (−196° C.). Mechanical refrigeration could also be employed in lieu of a cold temperature medium. In more sophisticated types of apparatus, cold temperature media such as a liquid hydrogen ($H_2$) bath (−253° C.) or a liquid helium (He) bath (−269° C.) could be used. Many other cold temperature media within the temperature range discussed herein are well known to those skilled in the art, and may be used in accordance with the present invention to provide a wide variety of possible temperatures for cold temperature bath 26.

Deposition cell 11 is evacuated by the vacuum pump through vacuum port 22 so as to create a low pressure vacuum within the deposition cell. The vacuum serves: (1) to cleanse the deposition cell of materials which are not to be deposited, (2) to provide the needed thermal insulation within the deposition cell, and (3) to avoid reactions between the heated portions (e.g., heating element 19) of the apparatus and air, such as oxidation reactions.

The extent of the vacuum will necessarily depend upon the particular chemical components and situation involved. The lower the pressure within deposition cell 11, the cleaner the deposition environment within the cell, resulting in the deposition of correspondingly less unwanted materials. For some applications where a clean environment is not too critical, pressures of $1 \times 10^{-5}$ torr, or perhaps even somewhat higher, may be adequate. However, where cleaner environments are needed, for example where only small amounts of the guest component are to be deposited with the host component, pressures smaller than $1 \times 10^{-5}$ torr (e.g., $1 \times 10^{-9}$ to $1 \times 10^{-10}$ torr) may be needed to provide such a clean environment. Of course, modifications to apparatus 10 shown in FIG. 1 would likely be needed to accommodate such smaller pressures.

It will be appreciated that since lower pressures require more sophisticated and expensive vacuum pumping apparatus, a trade-off must be made between the extent of the vacuum desired (and thus the cleanliness of the environment within the deposition cell) and the cost involved in achieving such a vacuum.

A solid host component, which is to provide the solid host medium for the solid solution, is placed into crucible 18. The solid host component within crucible 18 is vaporized by activating electrodes 20 so as to heat heating element 19 and crucible 18. One or more guest components to be included into the solid solution are vaporized, if not already in the vapor state, and the vaporized guest components are introduced into deposition cell 11 through apertures 16 of vapor supply conduit 14. The vaporized host component and vaporized guest components are then codeposited and condensed onto wall 12 of deposition cell 11 so as to form a composite or solid solution 28.

The selection of an appropriate host component is extremely important in the present invention. In contrast to the prior art inert gas matrices, the host component of the present invention preferably comprises a chemical compound or element (e.g., a metal, insulator, or semiconductor) which is a solid at temperatures at least as high as room temperature (e.g., about 20° C.). Indeed, host components having melting points much higher than room temperature may be used in accordance with the present invention.

The host component of the present invention may also have a freezing point lower than room temperature; however, it is generally undesirable to use host components having a freezing point significantly below about −40° C. This is because the resulting solid solutions, which would typically have somewhat similar freezing points, could not be easily stored and preserved except through low temperature refrigeration. Solid solutions having a freezing point between about −40° C. and room temperature could at least be stored and preserved using readily available refrigeration systems. Thus, it will be recognized that although solid solutions having freezing points below −40° C. may be prepared in accordance with the present invention, such solid solutions do not have the utility and versatility of those solid solutions which are stable above −40° C., and especially of those solid solutions which are stable at room temperature or higher.

Important criteria in the selection of an appropriate host component include the following: (1) the host component must be a solid, preferably at temperatures of at least as high as about −40° C. and more preferably at room temperature or higher; (2) it must be possible to generate the host component in the gaseous state (e.g., by heating and vaporizing a solid host component, or by generating the host component in gaseous form from a suitable precursor); and (3) the gaseous host component must be capable of deposition from the gaseous state onto a cold substrate so as to condense and form a solid polymeric or macromolecular structure.

There are a vast number of chemical compounds or elements which may be used as the host component in the present invention. For example, the host component may comprise:

chemical elements, such as metals (e.g., Sn, Cu, Se, and Te);

metal halides, such as alkali halides (e.g., CsX, where X is a halogen, and NaCl) and other metal halides (e.g., CuX, AgX, TlX, $HgX_2$, $PbX_2$, $CdX_2$, where X is a halogen, $BeF_2$, $MgF_2$, and $CaF_2$);

oxides (e.g., $Ga_2O_3$, $In_2O_3$, $Tl_2O$, $Sb_2O_3$, $Bi_2O_3$, $VO_2$, $MoO_2$, $WO_3$, TiO, SiO, GeO, SnO, PbO, $As_4O_6$, and $B_2O_3$);

boron nitride (BN);

chalcogenide glasses, i.e., amorphous crosslinked polymers formed combining one of the chalcogens: sulfur (S), selenium (Se), or tellurium (Te), with one or more of the following elements: phosphorus (P), arsenic (As), antimony (Sb), bismuth (Bi), cadmium (Cd), mercury (Hg), gallium (Ga), indium (In), thallium (Tl), silicon (Si), germanium (Ge), tin (Sn), and lead (Pb); and other compounds such as alkali metal nitrates, alkali metal cyanides, alkali metal metaborates, $CF_2$, SO, PN, Te, and $(SN)_x$.

It will be appreciated that the foregoing list of possible host components is given by way of example only, and that this list is not intended to be exhaustive. Indeed, it will be appreciated that many other compounds which exist as solids at about $-40°$ C. or above may be used in the preferable application of the present invention.

It will also be recognized that, in the present invention, multiple host components or mixtures of chemical compounds can be codeposited into a single solid structure so as to form a solid solution of multiple components. In such solid solutions, one or more guest components could also be incorporated into the solid solutions in accordance with the present invention. Multiple host components may be codeposited, for example, by placing more than one host component into crucible 18 or by placing the different host components into separate crucibles. Moreover, it will be recognized that, where two or more host components are not capable of being codeposited into a single solid structure, such host components may be used in the present invention to simultaneously make mixtures of different solid solutions by simultaneously codepositing each different host component with one or more guest components.

The guest components of the present invention comprise chemical compounds or elements which are generally immiscible with the chosen host component using chemical techniques known in the prior art. The guest components may be solids, liquids, or gases at room temperature.

The guest component is immiscible with the host component in the sense that the guest component is contained to a negligible extent within the host component under equilibrium conditions. In other words, substantially no appreciable amounts of the guest component would be found diffusing into the host component at even the most ideal of conditions. Thus, in the composite materials of the present invention, the guest and host components are intimately mixed in concentrations much greater than would exist at equilibrium. Surprisingly, upon incorporation of the guest component into the host component to form a solid solution in accordance with the present invention, the guest component becomes trapped within the host component such that little movement of the guest component is possible. Thus, in the solid solutions of the present invention, the guest component is trapped within the host component in a kinetically stable condition far from equilibrium.

Important criteria for the choice of one or more appropriate guest components include: (1) it must be possible to generate the guest component or components in the gaseous state (e.g., by heating and vaporizing the guest component or components, or by generating the guest component or components in gaseous form from a suitable precursor or precursors); and (2) the gaseous guest component or components must be capable of deposition onto a cold substrate so as to condense and form a stable solid solution with the host component. It will be appreciated that the selection of appropriate guest components will necessarily depend upon the intended use of the solid solution to be produced.

Sometimes, a particular guest component may be prepared by heating a precursor material which produces the guest component upon heating. In some instances, it is desirable to choose a guest component which will not react with the host component. In other instances, it may be desirable to choose a guest component which will react with the host component to form a new chemical structure.

Moreover, it will be appreciated that the number of different possible guest components for any given host component is large. By way of example only, it has experimentally been found that aromatic organic compounds may be satisfactorily used as guest components for purposes of the present invention where the host component is a metal halide.

Because the preferable host components of the solid solutions of the present invention are solids at temperatures of about $-40°$ C. or greater, the resulting solid solutions made by incorporating one or more guest components into the host component have generally also been found to be solids at corresponding temperatures. Thus, the solid solutions made from such host components according to the present invention are stable at temperatures of at least as high as about $-40°$ C., and often much higher, depending in large part upon the host component used. Except according to the techniques of the present invention, it will be readily recognized that the solid solutions of the present invention have not heretofore been prepared, since standard chemical techniques have been incapable of combining such normally immiscible components into a solid solution.

The present invention provides a method of "packaging" chemical compounds for subsequent use, release, transformation, or examination, that is, a method of isolating and preserving compounds which may be unstable in air, may have bad odors, may be toxic (such as radioactive or poisonous materials), may be highly reactive (such as reaction intermediates or compounds having a tendency to dimerize or polymerize) or corrosive, may be flammable, may be explosive in bulk, or may have other similar qualities which limit their use by conventional storage techniques.

Such chemical compounds are incorporated as guest components into a relatively chemically inert solid host component or "packaging component" in accordance with the present invention. The result is that these chemical compounds are entrapped, isolated, and preserved within the inert solid host component for future release, use, transformation, or examination, without decomposing or becoming unstable, without exhibiting their bad odor, without exhibiting their toxicity, without reacting prematurely or corrosively with themselves or other chemical compounds, without igniting, without exploding, or without exhibiting their other "peculiar" qualities.

For example, there are many drugs which are known to be air-sensitive. By isolating these drugs into a host component, these drugs can be preserved in stable form and can be released simply by swelling or dissolving the host component "package." Again by way of example, unstable compounds such as ozone may be suspended within a hot component (e.g., sodium chloride) and preserved in stable form for purposes of chemical oxidation. Such an ozone/sodium chloride solid solution could be used, for example, in the purification of water by merely dropping the ozone/sodium chloride solid into the water to be purified so that the ozone is released upon dissolution of the sodium chloride. Additionally, the trapped guest components may be observed and their response to chemical and physical stimuli recorded at room temperature or higher in the solid solutions of the present invention. Thus, the experimental utility of the solid solutions of the present invention for basic scientific research is also important.

From the foregoing, it will be appreciated that an important feature of the solid solutions of the present invention is that the guest component is actually trapped or imprisoned within the host component, and that the guest component is not merely mixed with the host component as an intimate micromixture of small particles. This novel feature distinguishes the solid solutions of the present invention over that prior art which relates to such micromixtures of various chemical components.

An important reaction condition to control while making solid solutions in accordance with the present invention is the temperature of wall 12 of deposition cell 11. Of course, the temperature of wall 12 is controlled by choosing an appropriate cold temperature medium for cold temperature bath 26.

Some important considerations in choosing an appropriate deposition temperature for a given solid solution to be prepared, include: (1) the deposition temperature should be low enough to condense the guest component molecules and the host component molecules from a gaseous state into a solid state; and (2) the deposition temperature should be low enought to minimize movement and translation of the guest molecules within the host component so as to prevent substantial aggregation of the guest molecules (unless such aggregation is desired). Other chemical properties, however, may dictate that the deposition temperature not be excessively low.

The actual temperature of the wall of the deposition cell will depend upon such factors as: (1) the rate at which the guest and host components are deposited on the wall (if the deposition rates are relatively rapid, a large temperature gradient may exist across the wall), (2) the thermal conductivity of the wall and the rate at which heat is dissipated through the wall, (3) the temperature of the vaporized guest and host components as they meet the wall, and (4) the heats of vaporization (or actually, the heats of condensation) of the guest and host components.

Where the main concern is to quench the translational movement of the guest molecules upon deposition so as to prevent aggregation of the guest molecules within the host component, the lowest possible deposition temperature should be achieved. Such low temperatures will slow down the movement of the guest molecules so as to provide a nearly or completely monomolecular dispersion of the guest molecules within the host component. In some applications, such a monomolecular dispersion is extremely desirable in terms of isolating the guest component as single molecules within the host component and in terms of the utility and experimental value of the resultant solid solutions. It will thus be appreciated that controlling the temperature of the wall of the deposition cell provides some control over the degree of aggregation of the guest component.

Monomolecular dispersion of the guest component within the host component may be desirable—for example, when the guest molecules would react with each other if brought together, and when such a reaction would be undesirable. Monomolecular dispersion would also be preferable where it is desirable to observe a certain guest component in isolation. For other applications of the present invention, monomolecular dispersion of the guest component within the host component may be unnecessary, or even undesirable. Thus, the deposition temperature should be carefully chosen so as to promote or inhibit monomolecular dispersion as desired. Thus, it is important to recognize that the optimum deposition temperature may not, in all cases, be the lowest possible temperature. Moreover, economic factors may result in the use of a temperature somewhat higher than the optimum deposition temperature.

It has been found that another important factor in minimizing translation and aggregation of the guest molecules within the host component upon deposition is the heat of vaporization of the host component and the guest components. Since the vaporized host component and guest components release their heat of vaporization as they condense onto the wall of the deposition cell to form the solid solution, the heat released encourages movement and therefore aggregation of the guest molecules within the host component. Thus, it has been found particularly desirable to choose a host component having a relatively low heat of vaporization.

Another factor related to minimizing translation and aggregation of the guest molecules within the host component is the temperature to which the host component and guest components must be heated in order to place them into a vapor state for subsequent deposition. If, for example, the host component has a high vaporization point, the vaporized host component will carry a significant amount of heat that will need to be dissipated by the cold wall of the deposition cell. If the wall cannot dissipate the heat quickly enough, translation and aggregation of the guest molecules may result.

Another important parameter to control in the manufacture of the solid solutions of the present invention is the rate at which each of the host and guest components are introduced and deposited onto the wall of the deposition cell. The optimum rates of deposition will, of course, depend upon the particular components involved. Since aggregation of the guest molecules within the host component will depend in part upon the ratio of the host component to the guest component and the ability of the host component to "trap" and isolate single molecules of the guest component upon deposition, the rates of deposition for each component should be optimized.

Solid solutions prepared in accordance with the present invention have been found to be stable under ordinary pressures and at temperatures of up to about 200° C. or higher without decomposing. The exact decomposition temperature of each solid solution will, of course, depend upon the properties of the solid host component (such as its melting point).

The solid solutions of the present invention have been found to be stable even above the vaporization temperatures of the various guest components incorporated into the solid solutions. Also, these solid solutions have been found to be stable under a vacuum, with the guest components remaining incorporated into the solid host component. Moreover, after being stored at room temperature for several months, no change in the structure or composition if the solid solutions prepared in accordance with the present invention could be detected. The foregoing demonstrates the long-term stability of the solid solutions of the present invention.

The present invention can also be used to modify the surface structure of a solid material (the solid material comprising one or more chemical components) for various purposes. For example, the methods of the present invention can be used to modify the surface of a solid material using a particular template material to modify the surface. Such surface modification is accomplished using substantially the same procedure disclosed herein for making solid solutions in accordance with the present invention.

Referring again to FIG. 1, one presently preferred method for modifying the surface structure of a solid material will be explained. Cold temperature bath 26 is prepared by introducing an appropriate cold temperature medium into vessel 24. Deposition cell 11 is evacuated by the vacuum pump through vacuum port 22 so as to create a low pressure vacuum within the deposition cell. A solid material (the surface of which is to be modified) is placed into crucible 18. The solid material within crucible 18 is vaporized by activating electrodes 20 so as to heat heating element 19 and crucible 18.

A template material (which is to modify the surface of the solid material) is vaporized, if not already in the vapor state, and the vaporized template material is introduced into deposition cell 11 through apertures 16 of vapor supply conduit 14. The vaporized material from crucible 18 and the vaporized template material are then codeposited and condensed onto wall 12 of deposition cell 11 such that the resulting solid material deposited on wall 12 has molecules of template material embedded in its surface.

The embedded molecules of template material are then removed from the surface of the solid material, leaving behind a modified surface structure. To accomplish this removal, the solid material deposited on wall 12 of deposition cell 11 is removed from the deposition cell and placed under a vacuum. The vacuum encourages escape of the molecules of the template material from the solid material, especially where the template material is a material which is normally gaseous or liquid at room temperature.

Alternatively, the molecules of the template material can be removed from the surface of the solid material by washing the surface with an appropriate solvent. The solvent used should have an affinity for the template molecules, but should not significantly disturb the configuration of the surface of the solid material. Thus, the solvent acts to pull away or even dissolve the template molecules from the surface of the solid material, while preserving the modified surface formed by the template molecules after removal.

It will be appreciated that there may be other techniques for removing the template molecules. For example, some or all of the template molecules might, with certain compounds, escape naturally into the air, if the solid material is allowed to stand for a sufficient length of time.

It will be appreciated that the same temperature, pressure, and other parameters given herein for making solid solutions in accordance with the present invention, are also applicable to the methods for modifying the surface structures of solid materials, and will thus not be reiterated. Indeed, the present invention may be used to both create a novel solid solution and to modify the surface of that solid solution so as to impart a particular structure to the surface of the solid solution.

The application of the present invention to modification of surfaces is an example of where monomolecular dispersion is desirable. By embedding the template molecules as single molecules over the surface of the solid material, footprints of single template molecules rather than of agglomerates of template molecules are formed. This is advantageous, for example, where the formed footprints are used as a means for changing the adsorption properties of the surface or for selective adsorption of the template material in a vapor detection type application.

In addition to vapor detection, the surface modifying techniques of the present invention may also have application in such areas a enantiomer electrodes, separations of racemic mixtures, specific catalysis, and for the detection of the presence of chemical substances. Moreover, by using the present invention to change the adsorption properties of solid materials, further changes in such properties as electrical resistance, photoconductivity, magnetic properties, and optical properties may result. Thus, by modifying surfaces in accordance with the present invention, a wide variety of applications are possible.

It will be recognized that, in practicing the present invention, the chemical nature of the guest component or components and of the host component or components, as well as the conditions under which codeposition is conducted, will determine the degree of incorporation of the guest components into the host components. If the guest component is incorporated into the solid structure of the host component, the guest component will usually also be deposited on the surface of the host component so as to modify the surface of the host component. Where the guest component is codeposited on the surface of the host component, however, the degree of incorporation of the guest component into the solid structure of the host component may vary. In some instances, the guest component may be deposited only on the surface of the host component. In other instances, the guest component may be deposited on the surface of the host component and also incorporated within a layer near the surface of the host component. Finally, deposition of the guest component onto the surface of the host component and complete incorporation of the guest component into the entire solid structure of the host component may be achieved.

The degree of incorporation of the guest component into the host component will depend upon the chemical nature of the guest and host components, and such conditions and factors as the rate of deposition, the deposition temperature, the temperature of the components before deposition, the heats of vaporization of the components, and other factors. Thus, it will be recognized that the degree of incorporation of the guest component into the host component, may, to some extent, be controlled by controlling these various conditions and factors.

The following examples are exemplary of novel solid solutions and surface modifications which have been made and accomplished using the present invention, but are given by way of illustration only. In these examples, various guest components were incorporated inside of the solid structure and/or onto the surface of various solid host components. From the foregoing, it will be recognized that both types of incorporation are within the scope of the present invention; it may be desirable to achieve one type of incorporation or both, depending upon the particular application.

EXAMPLE 1

The solid solution of Example 1 was prepared in accordance with the present invention using sodium chloride (NaCl) as the solid host component and benzene as the guest component. In Example 1, an apparatus substantially similar to apparatus 10 of FIG. 1 was utilized, employing the following experimental conditions:

Wall temperature of deposition cell = −196° C. (liquid nitrogen bath employed)
Deposition time = 25–30 minutes
Vacuum — 1 × 10⁻⁵ torr
Temperature of crucible = 940° C.–950° C.
Temperature of vaporized guest component = room temperature (about 22° C.)

In the preparation of the solid solution of Example 1, a liquid nitrogen ($N_2$) bath was placed in the insulated vessel surrounding the deposition cell so as to cool the wall of the deposition cell to about −196° C. The crucible was filled with sodium chloride salt and the deposition cell was evacuated by the vacuum pump to a pressure of about $1 \times 10^{-5}$ torr. The crucible was then heated to a temperature of about 940° C.–950° C. so as to vaporize the sodium chloride host component. Benzene vapor at room temperature was introduced simultaneously into the deposition cell. Codeposition of the sodium chloride and benzene was allowed to proceed for about 25–30 minutes. In Example 1, benzene was incorporated both into the sodium chloride solid and onto the sodium chloride surface.

The procedure used to determine whether benzene was deposited inside of the sodium chloride solid and/or onto the sodium chloride surface was as follows. The resulting sodium chloride material from Example 1 was vacuum pumped to remove any benzene incorporated onto the surface of the sodium chloride, and all volatile material removed from the surface of the sodium chloride was trapped over a suitable period of time and analyzed. The trapped volatile material was experimentally determined to be benzene.

After all of the volatile materials had been removed from the sodium chloride surface, the sodium chloride material was dissolved and analyzed spectrally for the presence of benzene. Benzene was found to be present in the sodium chloride solution, indicating that benzene had been incorporated into the solid sodium chloride. Similar procedures were used with respect to the other examples disclosed herein.

The molar ratio of sodium chloride to benzene inside of the solid solution (after the benzene deposited on the surface had been pumped away) was about 750 to 1. The stability of the benzene/sodium chloride solid solution of Example 1 was also experimentally determined. The benzene/sodium chloride solid solution was heated to temperatures of up to about 200° C. without decomposing, and there was no detectable change to the chemical composition and structure of the benzene/sodium chloride solid solution after storage for more than three months.

Figure 2:
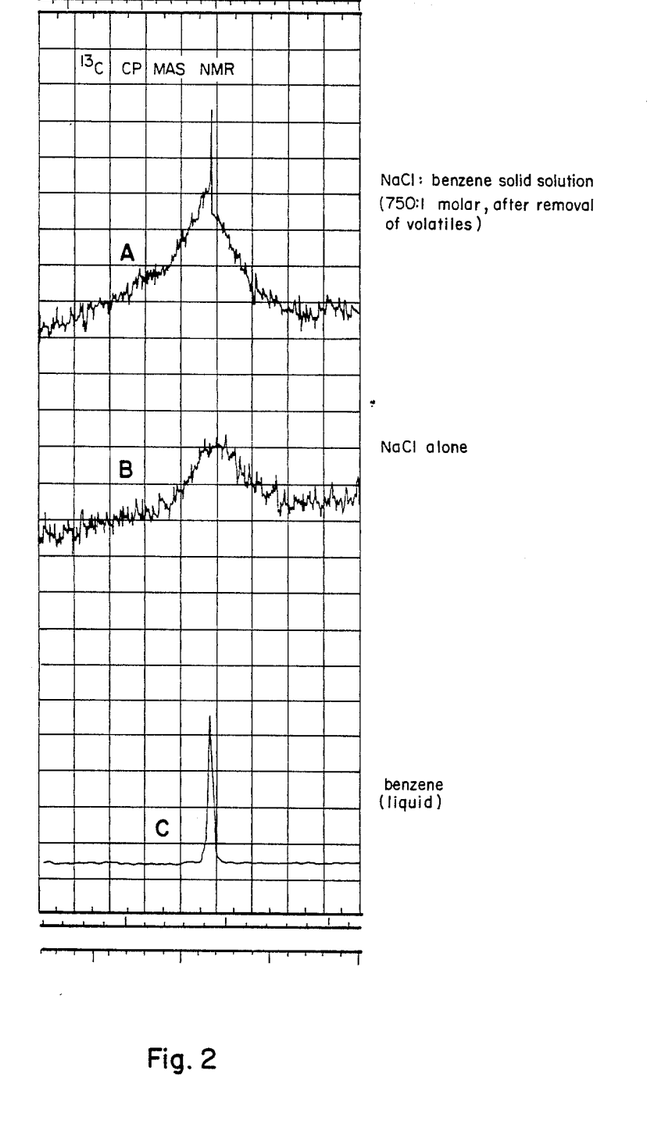
FIG. 2 illustrates room temperature $^{13}C$ NMR spectra obtained from benzene alone, sodium chloride alone, and a solid solution of benzene/sodium chloride prepared in accordance with the present invention.

After removing the volatile benzene molecules deposited on the surface of the sodium chloride by vacuum pumping the solid solution of Example 1, several nuclear magnetic resonance ("NMR") spectra were taken of the solid solution. These spectra are reproduced in FIGS. 2 and 3. The spectra illustrated in FIG. 2 are carbon-13 NMR ($^{13}C$ NMR) spectra taken at room temperature, with cross polarization and magic angle spinning. Spectrum A of FIG. 2 represents the benzene/sodium chloride solid solution of Example 1. For purposes of comparison, spectrum B of FIG. 2 was taken using sodium chloride alone; spectrum C was obtained from liquid benzene alone. As seen in FIG. 2, spectrum A of the benzene/sodium chloride solid solution of Example 1 shows that benzene was incorporated into the sodium chloride solid.

Figure 3:
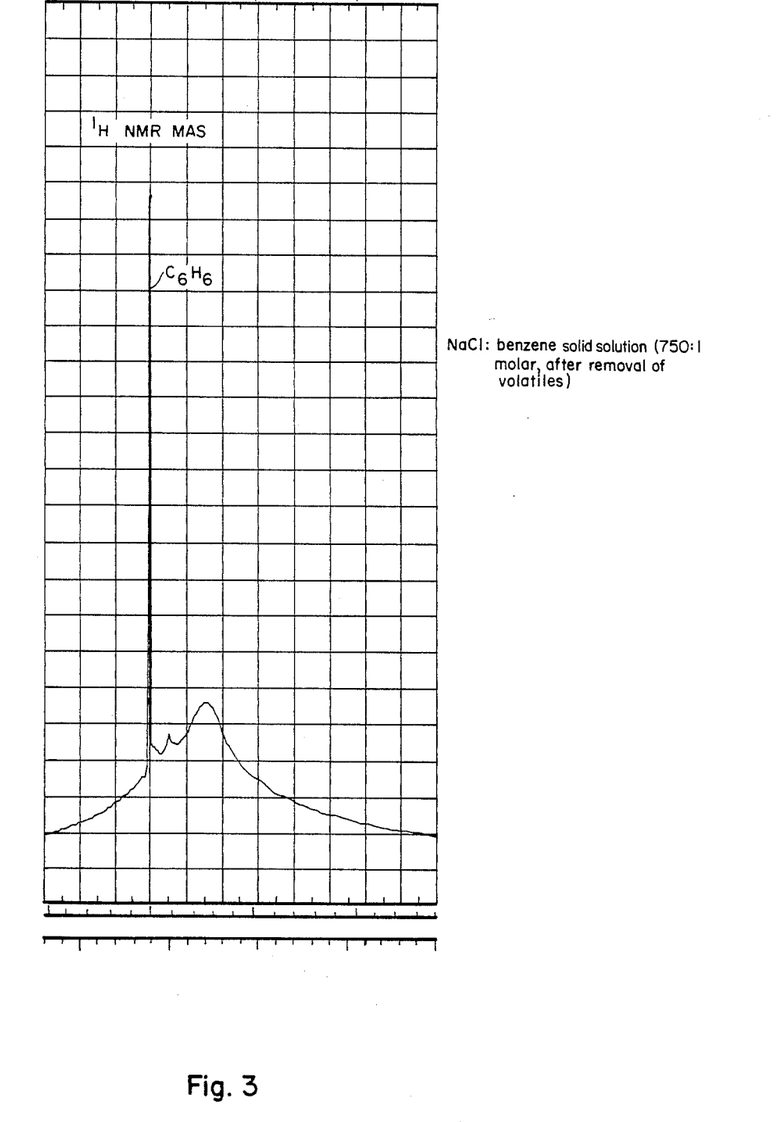
FIG. 3 illustrates a room temperature proton NMR spectrum of a solid solution of benzene/sodium chloride which was made in accordance with the present invention.

The spectrum illustrated in FIG. 3 is a proton NMR spectrum taken at room temperature with magic angle spinning. As seen in FIG. 3, the spectrum of the benzene/sodium chloride solid solution of Example 1 shows a strong absorption corresponding to the benzene protons, thus again indicating the presence of benzene inside of the sodium chloride solid.

EXAMPLES 2–6

The solid solutions of Examples 2–6 were prepared in accordance with the present invention using sodium chloride as the solid host component, and using the same reaction conditions and following the same experimental procedure as in Example 1 except that benzene was not the guest component used. A different guest component was used in each of Examples 2–6. These guest components are listed in Table I below, along with the indicated results as to whether incorporation of the guest component onto the surface and/or inside of the sodium chloride solid was achieved.

TABLE I

| | Solid Solutions With Sodium Chloride as the Host Component | | | |
|---|---|---|---|---|
| Example No. | Guest Component | Incorporation of the Guest Component Onto the Surface of the Sodium Chloride Solid? | Incorporation of the Guest Component Inside of The Sodium Chloride Solid? | Molar Ratio of Sodium Chloride to Incorporated Guest Component |
| 2 | Toluene | Yes | Yes | 1600:1 |
| 3 | Naphthalene | Yes | Yes | 960:1 |
| 4 | Dodecamethyl-cyclohexasilane | Yes | Yes | |
| 5 | P—Dichlorobenzene | Yes | Yes | 840:1 |
| 6 | Diphenylmethane | Yes | Yes | 1340:1 |

As seen from Table I, in Examples 2–6, toluene, naphthalene, dodecamethylcyclohexasilane, p-dichlorobenzene, and diphenylmethane, were incorporated both onto the surface of the sodium chloride and into the sodium chloride solid. In these examples wherein the guest components were incorporated into the sodium chloride solid itself, the molar ratio of the sodium chloride host component to each respective guest component (after vacuum pumping off the volatile guest component molecules from the sodium chloride surface) was greater than 800 to 1. It should be mentioned, however, that no attempt was made to optimize these molar ratios, and that molar ratios much smaller are likely possible. The stability of the solid solutions made in these examples was tested at temperatures of up to about 200° C. These solid solutions were found to be stable at such temperatures and did not decompose after storage for several months.

Figure 4:
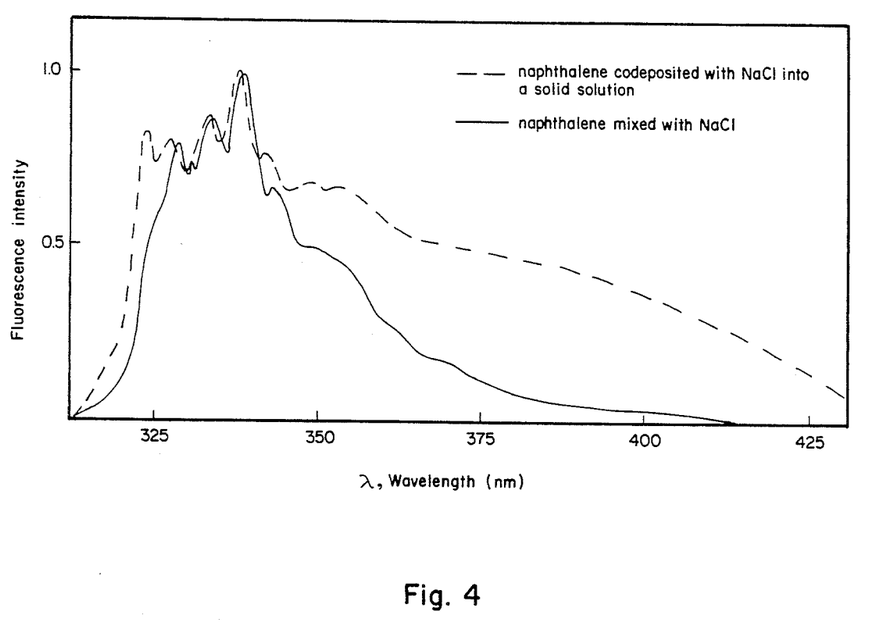
FIG. 4 illustrates room temperature fluorescence spectra of a solid solution of naphthalene/sodium chloride which was made in accordance with the present invention and a simple mixture of sodium chloride and naphthalene crystals.

A fluorescence spectrum was taken of the solid solution of Example 3, after removing the volatile naphthalene molecules deposited on the surface of the sodium chloride by vacuum pumping the solid solution of Example 3. This spectrum, along with a fluorescence spectrum of a simple mixture of sodium chloride and naphthalene crystals (for comparison purposes), are reproduced in FIG. 4. The fluorescence spectra of FIG. 4 were taken at room temperature. The dashed line represents the spectrum of the naphthalene/sodium chloride solid solution of Example 3, while the solid line represents the spectrum of the simple mixture of sodium chloride and naphthalene. As seen in FIG. 4, there are substantial differences in the two spectra, strongly suggesting that the naphthalene in the solid solution of Example 3 is imbedded within the sodium chloride not solely as large microcrystals, but as much smaller units.

EXAMPLES 7-12

Examples 7-12 involve modifications of the surface structure of sodium chloride which were achieved in accordance with the present invention. These surface modifications were achieved using the same reaction conditions and following the same experimental procedure as in Example 1, except that instead of using benzene as a guest component, various other guest components or template materials were used. A different template material was used in each of Examples 7-12. These template materials are listed in Table II below, along with the indicated results as to whether the template material was incorporated onto the surface and/or inside of the sodium chloride solid.

TABLE II

Surface Modifications of Sodium Chloride

| Example No. | Template Material | Incorporation of the Template Material Onto the Surface of the Sodium Chloride Solid? | Incorporation of the Template Material Inside of The Sodium Chloride Solid? |
|---|---|---|---|
| 7 | Chlorobenzene | Yes | No |
| 8 | Anisole | Yes | No |
| 9 | Acetophenone | Yes | No |
| 10 | Pyrrole | Yes | No |
| 11 | Phenol | Yes | No |
| 12 | P—Fluorophenol | Yes | No |

As seen in Table II, in Examples 7-12, chlorobenzene, anisole, acetophenone, pyrrole, phenol, and p-fluorophenol were incorporated onto the surface of the sodium chloride, but not inside of the sodium chloride solid in significant amounts. Thus, these examples are given to show the surface modifying application of the present invention where incorporation into the solid host material is not experienced. It is believed that the reason that the template materials of Examples 7-12 were not incorporated into the sodium chloride solid may be related to the relatively high polarity or dipole moment of those template materials. (The guest components of Examples 1-6 which were successfully incorporated into the sodium chloride solid are relatively nonpolar.)

It should be recognized, however, that although the template materials of Examples 7-12 were not incorporated into the sodium chloride solid in these examples, such incorporation may indeed be possible by changing the reaction conditions, e.g., by using a lower deposition temperature than that used in Examples 7-12 ($-196°$ C.).

In Examples 7-12, the template material deposited on the sodium chloride surface was removed by vacuum pumping the sodium chloride solid. The resulting sodium chloride surface was modified by the impressions left by each respective template material.

EXAMPLES 13-21

The toluene/sodium chloride solid solution of Example 2 was vacuum pumped to remove the toluene molecules on the sodium chloride surface, thereby yielding a modified surface. A modified sodium chloride surface was also prepared by vacuum pumping off the phenol molecules which were deposited on the surface of the sodium chloride solid in Example 11. Tests were then conducted to measure the adsorption properties of the modified sodium chloride surfaces from Examples 2 and 11. In these tests, the sodium chloride solids were reduced in particle size and the adsorption properties of the modified surfaces of these solids for different chemical compounds were compared to those of sodium chloride salt deposited alone. The relative adsorption (adsorption of the different chemical compounds by the modified sodium chloride surfaces of the present invention versus the normal adsorption of those compounds by unmodified sodium chloride) was measured for various chemical compounds. The results of these experiments are reported as Examples 13-21 in Table III below.

TABLE III

Adsorption Properties of Modified Sodium Chloride Surfaces

| Example No. | Compound Adsorbed | Template Material Codeposited with the Sodium Chloride Salt to Modify the Surface in Accordance with the Present Invention | Molar Ratio of the Sodium Chloride Salt to the Template Material Deposited on the Surface of the Solid Solution Before Removal of the Template Material | Size of the Sodium Chloride Particles | Relative Adsorption (Modified Sodium Chloride vs. Normal Sodium Chloride) |
|---|---|---|---|---|---|
| 13 | Phenol | Phenol | 120 | Coarsely Ground | 2.63 |
| 14 | 2-Methylphenol | Phenol | 120 | Coarsely Ground | 2.67 |
| 15 | 2,6-Dimethylphenol | Phenol | 120 | Coarsely Ground | 3.11 |
| 16 | Phenol | Phenol | 120 | 400 Mesh | 1.64 |
| 17 | 2,6-Dimethylphenol | Phenol | 120 | 400 Mesh | 1.70 |
| 18 | Phenol | Phenol | 590 | Coarsely Ground | 2.16 |
| 19 | 2,6-Dimethylphenol | Phenol | 590 | Coarsely Ground | 1.63 |
| 20 | Phenol | Toluene | 1600 | Coarsely Ground | 0.48 |
| 21 | Toluene | Toluene | 1600 | Coarsely | 0.57 |

TABLE III-continued

| | | Adsorption Properties of Modified Sodium Chloride Surfaces | | | |
|---|---|---|---|---|---|
| Example No. | Compound Adsorbed | Template Material Codeposited with the Sodium Chloride Salt to Modify the Surface in Accordance with the Present Invention | Molar Ratio of the Sodium Chloride Salt to the Template Material Deposited on the Surface of the Solid Solution Before Removal of the Template Material | Size of the Sodium Chloride Particles Ground | Relative Adsorption (Modified Sodium Chloride vs. Normal Sodium Chloride) |

As seen from Table III, the absorption properties of sodium chloride for various chemical compounds were dramatically affected when phenol or toluene was incorporated onto the surface of the sodium chloride crystal lattice in accordance with the present invention and subsequently removed to modify the sodium chloride surface. For example, as seen from Example 23, the modified sodium chloride from Example 11 provided a material which absorbed over three times as much 2,6-dimethylphenol as normal sodium chloride. Conversely, as seen from Example 28, the modified sodium chloride from Example 2 provided a material which adsorbed less than one-half as much phenol as normal sodium chloride.

It may be further seen from Table III that the adsorption properties of the modified sodium chloride tested in Examples 13–19 became closer to the actual adsorption properties of normal sodium chloride as the particle size of the sodium chloride was reduced (compare, for example, Example 13 with Example 16, and Example 15 with Example 17) and as the molar ratio of sodium chloride to the template material initially deposited on the surface of the sodium chloride to modify the sodium chloride surface was increased (compare, for example, Example 13 with Example 18, and Example 15 with Example 19).

Thus, the results of Examples 13–21 reported in Table III suggest that the present invention may be used to increase or decrease the adsorption properties of solid materials (such as sodium chloride) for different chemical compounds as desired, by careful selection of the template material initially incorporated onto the surface of the solid material, by adjusting the particle size to which the solid material is reduced, and/or by adjusting the molar ratio of the solid material to the template material initially deposited on the surface of the solid material. (The molar ratio can be controlled, for example, by controlling the relative rates of introduction and subsequent deposition of each respective component within the deposition cell.)

Examples 13–21 suggest that selective adsorption properties can be imparted to the surfaces of such materials as sodium chloride using the present invention. Modification of the surface adsorption properties would find application in such areas as vapor detectors, enantiomer electrodes, separations of racemic mixtures, and specific catalysis. In view of the foregoing Examples 13–21, other chemical and physical properties of solid materials are also anticipated to be affected by modifying their surfaces in accordance with the present invention.

EXAMPLES 22–26

The solid solutions of Examples 22–26 were prepared in accordance with the present invention using cesium iodide (CsI) as the solid host component. The reaction conditions used and the experimental procedure followed were identical to those for Example 1, with the following exceptions. In each of Examples 22–26, the crucible was heated to a temperature of about 770° C.–780° C. so as to vaporize the cesium iodide host component. In Example 23, a three molar (3M) solution of calcium chloride ($CaCl_2$) in ice water having a temperature of about $-22°$ C. was placed in the insulated vessel surrounding the deposition cell so as to provide a deposition temperature of about $-22°$ C. at the wall of the deposition cell. In Example 25, a dry ice/acetone bath ($CO_2/CH_3COCH_3$) having a temperature of about $-77°$ C. was placed in the insulated vessel surrounding the deposition cell so as to provide a deposition temperature of about $-77°$ C. Moreover, in Example 25, the guest component (phenol) was preheated to about 100° C. so as to minimize the presence of dimers in the vaporized host component, and deposition was allowed to proceed for about two hours. A different guest component was used in each of Examples 22–26. These guest components are listed and the results of incorporating each respective guest component into the cesium iodide solid are reported in Table IV below.

TABLE IV

| | Solid Solutions with Cesium Iodide as the Host Component | |
|---|---|---|
| Example No. | Guest Component | Incorporation of the Guest Component Inside of the Cesium Iodide Solid? |
| 22 | Naphthalene | Yes |
| 23 | Dodecamethyl-Cyclohexasilane | Yes |
| 24 | Chlorobenzene | Yes |
| 25 | Phenol | Some Incorporation |
| 26 | 2,6-Dichlorophenol | Yes |

As may be seen from Table IV, in Examples 22–24 and 26, naphthalene, dodecamethylcyclohexasilane, chlorobenzene, and 2,6-dichlorophenol were incorporated directly into the cesium iodide solid in significant quantities. Phenol was incorporated into the cesium iodide solid in relatively small quantities as seen from Example 25. Indeed, in Examples 22–24 and 26, it was found that the molar ratio of the cesium iodide host component to each respective guest component (after pumping off the volatile guest component molecules deposited on the cesium iodide surface) was on the order of about 200 to 1.

EXAMPLES 27–29

The solid solutions of Examples 27–29 were prepared in accordance with the present invention using copper (I) chloride (CuCl) as the solid host component. The reaction conditions used and the experimental procedure followed were identical to those for Example 1, except that in each of Examples 27–29, the crucible was heated to a temperature of about 420° C.–430° C. so as to vaporize the copper chloride host component. A different guest component was used in each of Examples 27-29. These guest components are listed and the results of incorporating each respective guest component into the copper chloride solid are reported in Table V below.

TABLE V

| | Solid Solutions with Copper (I) Chloride as the Host Component | |
|---|---|---|
| Example No. | Guest Component | Incorporation of the Guest Component Inside of the Copper Chloride Solid? |
| 27 | Naphthalene | Yes - to very high concentrations |
| 28 | Chlorobenzene | Yes - to very high concentrations |
| 29 | Phenol | Yes - to fairly high concentrations |

As seen from Table V, in Examples 27-29, naphthalene, chlorobenzene, and phenol were all successfully incorporated into the solid structure of copper chloride. Indeed, the naphthalene and chlorobenzene were incorporated into the copper chloride salt at very high concentrations; the molar ratio of the copper chloride host component to each of naphthalene and chlorobenzene, was on the order of about 100 to 1.

Since no attempt was made to optimize the molar ratio in these experiments, it is anticipated that molar ratios even less than 100 to 1 may be achieved using the present invention. Moreover, phenol was successfully incorporated into the copper chloride salt crystal in fairly high concentrations.

A comparison of Tables IV and V with Tables I and II shows that much greater success was had in incorporating various guest components into the cesium iodide solid and the copper chloride solid than into the sodium chloride solid. It is believed that one reason for this result may be the fact that sodium chloride has a relatively high heat of vaporization when compared to cesium iodide and copper (I) chloride.

EXAMPLES 30-32

Examples 30-32 relate to a series of tests in which the surface structure of tellurium (Te) was modified in accordance with the present invention. Example 30 is directed to a standard control; thus, in this example, tellurium was deposited alone. In Example 31, tellurium and copper (I) chloride were codeposited, and in Example 32, tellurium, copper (I) chloride, and water were codeposited.

As with the other examples, an apparatus substantially similar to apparatus 10 of FIG. 1 was utilized. A liquid nitrogen bath was placed in the insulated vessel surrounding the deposition cell so as to cool the wall of the deposition cell to about $-196°$ C. In example 30, the crucible was filled with 0.2 grams of tellurium. In Examples 31 and 32, a divided crucible was used, and 0.2 grams of tellurium were placed in one side of the crucible, while 0.0787 grams of copper (I) chloride were placed in the other side of the divided crucible in Example 31 and 0.0600 grams of copper (I) chloride were placed in the other side of the divided crucible in Example 32. The deposition cell was then evacuated by the vacuum pump to a pressure of about $1 \times 10^{-4}$ torr. The crucible was then heated to a temperature of about $525°-575°$ C. so as to vaporize the tellurium and copper (I) chloride host components. In Example 32 only, water vapor at a pressure of about $1 \times 10^{-2}$ torr was heated to a temperature of about 100° C. and introduced simultaneously into the deposition cell.

Deposition was allowed to proceed in each of Examples 30-32 for about 20 minutes. The thickness of the deposited films was not exactly measured, but was estimated to be from about 0.5 microns to about 5 microns thick.

Each of the films of Examples 30-32 was vacuum-pumped so as to remove all volatiles (including the water deposited with the film of Example 32). The electrical resistance across the films of Examples 30-32 was then measured (1) under a vacuum, (2) in the presence of a water atmosphere of about 16 torr, (3) in the presence of a methanol atmosphere of about 80 torr, and (4) in the presence of an acetone atmosphere of about 120 torr. The ratio of the resistance measured under each of the water, methanol, and acetone atmospheres to the resistance measured under the vacuum was calculated and this data is reported in Table VI below.

TABLE VI

| | Resistance Ratios | | |
|---|---|---|---|
| Example No. | $H_2O$ (16 torr): vacuum | $CH_3OH$ (80 torr): vacuum | Acetone (120 torr): vacuum |
| 30 | 1.18 | 1.07 | 1.06 |
| 31 | 1.70 | 1.01 | 1.03 |
| 32 | 1.49 | 1.37 | 1.23 |

As seen from Table VI, in Examples 31-32, codeposition of tellurium and copper (I) chloride, and codeposition of tellurium, copper (I) chloride and water, respectively, resulted in a substantial increase in the electrical resistance of the tellurium film, thereby indicating that the surface structure of the tellurium film in Examples 31 and 32 had been modified. It is believed that the higher resistance ratio is due to the fact that a greater amount of water, methanol, or acetone vapor was adsorbed at the surface of each film. In the film of Example 32, the resistance ratios for the methanol atmosphere: vacuum and acetone atmosphere: vacuum were considerably increased over the corresponding resistance ratios of Examples 30-31. Thus, from Table VI, it appears that the modified surface formed in Example 32, was more selective for the larger methanol and acetone molecules.

From the foregoing, it will be appreciated that the present invention provides methods for making untold numbers of solid solutions which have heretofore not been possible using conventional chemical techniques. Additionally, it will be appreciated that the present invention provides methods for modifying the surfaces of solid materials so as to modify properties such as the adsorption properties of the solid materials. It will be appreciated that since the present invention involves such novel solid solutions and methods, it is difficult to formulate terminology to describe these novel chemical advancements. Thus, the terminology used herein should be given the broadest interpretation which will correspond to the intent of the disclosure of the present invention.

The present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within their scope.

What is claimed and desired to be secured by U.S. Letters Patent is:

1. A method of making composites from chemical components which are not appreciably miscible under equilibrium conditions, the method comprising the steps of:
   providing a cold substrate;
   generating a vapor of a host component which is generally a solid at temperatures of at least as high as about −40° C.;
   generating a vapor of a guest component which is not appreciably miscible with the host component under equilibrium conditions; and
   codepositing the host component vapor and the guest component vapor on the cold substrate such that the guest component is incorporated into the host component in concentrations greater than those present under equilibrium conditions, the host component and the guest component condensing on the cold substrate to form a composite which is stable at temperatures of at least as high as about −40° C.

2. A method as defined in claim 1 wherein the temperature of the cold substrate is within the range of about −273° C. to about −20° C.

3. A method as defined in claim 1 wherein the temperature of the cold substrate is sufficiently low enough to prevent substantial translational movement and agglomeration of guest component molecules within the host component upon condensation of the host component and the guest component on the cold substrate.

4. A method as defined in claim 1 wherein the composite produced is characterized by a substantially monomolecular dispersion of the guest component in the host component.

5. A method as defined in claim 1 wherein the host component is generally a solid at temperatures of at least as high as about 0° C.

6. A method as defined in claim 1 wherein the composite produced is stable at temperatures of about 20° C. or greater.

7. A method as defined in claim 1 wherein the host component is a metal halide.

8. A method as defined in claim 1 wherein the host component is selected from the group consisting of NaCl, CuCl, and CsI.

9. A method as defined in claim 1 wherein the guest component is relatively volatile at room temperatures.

10. A method as defined in claim 1 wherein the guest component is an aromatic organic compound.

11. A method as defined in claim 1 wherein the guest component is selected from the group consisting of benzene, substituted benzene compounds, phenols, substituted phenols, naphthalene, and substituted naphthalene compounds.

12. A method as defined in claim 1 wherein the molar ratio of the host component to the guest component in the composite is at least about 100 to 1.

13. A method of making composites from chemical components which are not appreciably miscible under equilibrium conditions, the method comprising the steps of:
   providing a cold substrate;
   generating a vapor of a host component which is generally a solid at temperatures of at least as high as about 20° C.;
   generating a vapor of a guest component which is not appreciably miscible with the host component under equilibrium conditions; and
   codepositing the host component vapor and the guest component vapor on the cold substrate such that the guest component is incorporated into the host component so as to be kinetically stable within the host component, the host component and the guest component condensing on the cold substrate to form a composite which is stable at temperatures of at least as high as about 20° C.

14. A method of making composites from chemical components which are not appreciably miscible under equilibrium conditions, the method comprising the steps of:
   providing a cold substrate;
   generating a vapor of a host component which is generally a solid at temperatures of at least as high as about the temperature of dry ice;
   generating a vapor of a guest component which is not appreciably miscible with the host component under equilibrium conditions; and
   codepositing the host component vapor and the guest component vapor on the cold substrate such that the guest component is incorporated into the host component in concentrations greater than those present under equilibrium conditions, the host component and the guest component condensing on the cold substrate to form a composite which is stable at temperatures of at least as high as about the temperature of dry ice.

15. A method of making composites from chemical components which are not appreciably miscible under equilibrium conditions, the method comprising the steps of:
   providing a cold substrate;
   generating a vapor of a host component which is generally a solid at temperatures of at least as high as about −40° C.;
   generating a vapor of a guest component which is not appreciably miscible with the host component under equilibrium conditions; and
   codepositing the host component vapor and the guest component vapor on the cold substrate such that the guest component is incorporated into the host component in concentrations greater than those present under equilibrium conditions, the host component and the guest component condensing to form a composite on the cold substrate with minimal translational movement and agglomeration of the guest component molecules within the host component.

16. A method as defined in claim 15 wherein the temperature of the cold substrate is within the range of about −273° C. to about −20° C. and wherein the exact temperature of the cold substrate is controlled so as to control the extent of the translational movement and agglomeration of the guest component molecules within the host component.

17. A method of making solid solutions from chemical components which are not appreciably miscible under equilibrium conditions, the method comprising the steps of:
   providing a cold substrate having a temperature within the range of about −273° C. to about −190° C.;

generating a vapor of a host component which is generally a solid at temperatures of at least as high as about 20° C.;

generating a vapor of a guest component which is not appreciably miscible with the host component under equilibrium conditions; and codepositing the host component vapor and the guest component vapor on the cold substrate such that the guest component is incorporated into the host component in concentrations greater than those present under equilibrium conditions, the host component and the guest component condensing on the cold substrate to form a solid solution which is stable at temperatures of at least as high as about 20° C.

18. A method of modifying the surface structure of a solid material, the method comprising the steps of:

providing a cold substrate;

generating a vapor of a first material which is generally a solid at temperatures of at least as high as about −40° C.;

generating a vapor of a second material which is to provide a template for modifying the surface of the first material;

codepositing the first material vapor and the second material vapor on the cold substrate, the first material and the second material condensing on the cold substrate to form a solid wherein molecules of the second material attach to the surface of the first material; and removing the molecules of the second material from the surface of the first material, thereby leaving a modified surface on the first material.

19. A method as defined in claim 18 wherein the temperature of the cold substrate is within the range of about −273° C. to about −20° C.

20. A method as defined in claim 18 wherein the temperature of the cold substrate is sufficiently low enough to provide a substantially monomolecular dispersion of the molecules of the second material on the surface of the first material in the codepositing step.

21. A method as defined in claim 18 wherein the first material is generally a solid at temperatures of at least as high as about 20° C.

22. A method as defined in claim 18 wherein the second material is not appreciably miscible with the first material under equilibrium conditions.

23. A method as defined in claim 18 wherein removal of the molecules of the second material from the surface of the first material is enhanced by subjecting the molecules of the second material to a reduced pressure.

24. A method as defined in claim 18 wherein removal of the molecules of the second material from the surface of the first material is enhanced by washing the surface of the first material with a solvent.

25. A method as defined in claim 18 wherein the first material comprises tellurium and copper (I) chloride and wherein the second material comprises water.

26. A method of packaging chemicals so as to isolate them from the surrounding environment, the method comprising the steps of:

providing a cold substrate;

generating a vapor of a packaging component which is generally a solid at temperatures of at least as high as about −40° C.;

generating a vapor of a guest component which is not appreciably miscible with the packing component under equilibrium conditions; and codepositing the packaging component vapor and the guest component vapor on the cold substrate, the packing component and the guest component condensing on the cold substrate to form a solid solution wherein the guest component is trapped within the packaging component so as to be kinetically stable within the packaging component.

27. A method as defined in claim 26 further comprising the step of releasing the guest component from the packaging component by dissolving the packaging component.

28. A method as defined in claim 26 wherein the guest component is unstable in air.

29. A method as defined in claim 26 wherein the guest component has bad odor.

30. A method as defined in claim 26 wherein the guest component is toxic.

31. A method as defined in claim 26 wherein the guest component is highly reactive.

32. A method as defined in claim 26 wherein the guest component is corrosive.

33. A method as defined in claim 26 wherein the guest component is flammable.

34. A method as defined in claim 26 wherein the guest component is a material which is explosive in bulk.

35. A method as defined in claim 26 wherein the guest component is encapsulated by the packaging component so as to substantially prevent contact between the guest component and the surrounding atmosphere.

36. A method of making composites from chemical components which are not appreciably miscible under equilibrium conditions, the method comprising the steps of:

providing a cold substrate:

generating a vapor of an inorganic salt which is generally a solid at temperatures of at least as high as about −40° C.;

generating a vapor of a guest component which is not appreciably miscible with the inorganic salt under equilibrium conditions; and codepositing the inorganic salt vapor and the guest component vapor on the cold substrate such that the guest component is incorporated into the inorganic salt in concentrations greater than those present under equilibrium conditions, the inorganic salt and the guest component condensing on the cold substrate to form a composite which is stable at temperatures of at least as high as about −40° C.

37. A method as defined in claim 36 wherein the guest component is an organic guest component.

38. A method as defined in claim 36 wherein the inorganic salt is a metal halide.

39. A method of making composites from chemical components which are not appreciably miscible under equilibrium conditions, the method comprising the steps of:

providing a cold substrate;

generating a vapor of a host component which is generally a solid at temperatures of at least as high as about −40° C.;

generating a vapor of an organic guest component which is not appreciably miscible with the host component under equilibrium conditions; and codepositing the host component vapor and the organic guest component vapor on the cold substrate such that the organic guest component is incorporated into the host component in concentrations greater than those present under equilibrium conditions, the host component and the organic guest component condensing on the cold substrate to form a composite which is stable at temperatures of at least as high as about −40° C.

40. A method of making composites from chemical components which are not appreciably miscible under equilibrium conditions, the method comprising the steps of:

providing a cold substrate;

generating a vapor of a host component which is generally a solid at temperatures of at least as high as about −40° C.;

generating a vapor of an organic guest component which is not appreciably miscible with the host component under equilibrium conditions, the organic guest component being a phenol or a substituted phenol; and codepositing the host component vapor and the organic guest component vapor on the cold substrate such that the organic guest component is incorporated into the host component is concentrations greater than those present under equilibrium conditions, the host component and the organic guest component condensing on the cold substrate to form a composite which is stable at temperatures of at least as high as about −40° C.

* * * * *

UNITED STATES PATENT AND TRADEMARK OFFICE
CERTIFICATE OF CORRECTION

PATENT NO. :  4,599,462

DATED     :   July 8, 1986

INVENTOR(S) :  Josef Michl

It is certified that error appears in the above-identified patent and that said Letters Patent is hereby corrected as shown below:

Column 2, line 21, "if the fact" should be --is the fact--
Column 3, line 25, "guests components" should be --guest components--
Column 8, line 58, "hot component" should be --host component--
Column 10, line 58, "if the" should be --of the--

Column 26, line 7, "is concentrations" should be --in concentrations--

Signed and Sealed this

Second Day of December, 1986

Attest:

DONALD J. QUIGG

Attesting Officer

Commissioner of Patents and Trademarks

UNITED STATES PATENT AND TRADEMARK OFFICE
CERTIFICATE OF CORRECTION

PATENT NO. : 4,599,462
DATED : July 8, 1986
INVENTOR(S) : Josef Michl

It is certified that error appears in the above-identified patent and that said Letters Patent is hereby corrected as shown below:

Column 12, line 5, "areas a" should read -- areas as --.

Signed and Sealed this

Twenty-fourth Day of March, 1987

Attest:

DONALD J. QUIGG

Attesting Officer     Commissioner of Patents and Trademarks